United States Patent [19]
Glamkowski et al.

[11] 4,186,199
[45] Jan. 29, 1980

[54] INDOLO-,1,2-DIHYDROINDOLO-, AND 1,2,6,7-TETRAHYDROINDOLO [1,7-AB][1,5] BENZODIAZEPINES

[75] Inventors: Edward J. Glamkowski, Warren; James M. Fortunato, Somerville, both of N.J.

[73] Assignee: American Hoechst Corporation, Bridgewater, N.J.

[21] Appl. No.: 956,904

[22] Filed: Nov. 2, 1978

[51] Int. Cl.² .................. A61K 31/62; A61K 31/625; C07D 487/04
[52] U.S. Cl. ........................ 424/232; 260/326.5 B; 260/326.9; 260/326.11 R; 424/274
[58] Field of Search ...................... 260/326.5 B, 326.9; 424/274, 232

[56] References Cited

U.S. PATENT DOCUMENTS

| 3,642,822 | 2/1972 | Hester ......................... 260/326.5 B |
| 4,039,558 | 8/1977 | van der Burg .................. 260/326.5 B |

FOREIGN PATENT DOCUMENTS 1464432  2/1977  United Kingdom.

Primary Examiner—Alton D. Rollins
Assistant Examiner—M. C. Eakin
Attorney, Agent, or Firm—Curtis, Morris & Safford

[57] ABSTRACT

What is disclosed are

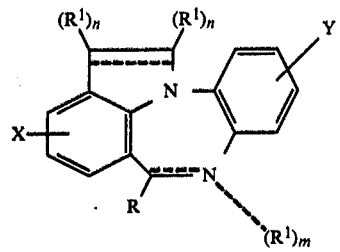

wherein
X is hydrogen, halogen or trifluoromethyl;
Y is hydrogen, halogen or trifluoromethyl;
R is hydrogen, loweralkyl, cycloalkyl, phenyl, halophenyl, furyl, pyridinyl, 4-methylpiperazin-1-ylethyl or phenylloweralkyl;
$R^1$ is hydrogen;
n and m are independently 0 or 1, but n is not 0 when m is 1, and the bonds between ring positions 1 and 2 and between positions 6 and 7 are respectively saturated when n and m are 1 and are unsaturated when n and m are 0;

pharmaceutically acceptable acid addition salts thereof; methods of preparing said compounds; pharmaceutical compositions including said compounds; methods of treatment using the compounds; and intermediates therefor.

These compounds are useful as analgesic and anti-inflammatory agents, as well as intermediates for the preparation of other pharmaceutically active compounds.

27 Claims, No Drawings

INDOLO-,1,2-DIHYDROINDOLO-, AND 1,2,6,7-TETRAHYDROINDOLO [1,7-AB][1,5] BENZODIAZEPINES

This invention relates to benzodiazepins and more particularly to indolo-, 1,2-dihydroindolo-, and 1,2,6,7-tetrahydroindolo[1,7-ab][1,5]benzodiazepins and their physilogically tolerable acid addition salts, which are useful as analgesic and anti-inflammatory agents as well as intermediates for the preparation of other pharmaceutically active compounds, to methods of treatment with pharmaceutically effective amounts thereof, to pharmaceutical composition cntaining such compounds as essential active ingredients, to methods of preparing such compounds, and to intermediates therefor.

To the best of our knowledge, the compounds of this invention have not heretofore been described or suggested. Riva et al., in U.S. Pat. No. 4,013,679, disclose compounds of the formula

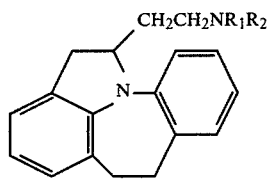

which are reported to possess antidepressant activity. But these compounds are substantially different from those of the present invention.

As a first embodiment, the present invention embraces compounds which may be depicted by the general formula

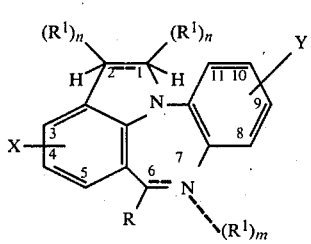

wherein
X is hydrogen or halogen;
Y is hydrogen, halogen or trifluoromethyl;
R is hydrogen, loweralkyl, cycloalkyl, phenyl, halophenyl, furyl or phenyllower alkyl;
$R^1$ is hydrogen;
n and m are independently 0 or 1, but n is not 0 when m is 1, and the bonds between positions 1 and 2 and between positions 6 and 7 are respectively saturated when n and m are 1 and are unsaturated when n and m are 0; and physiologically acceptable salts thereof.

In the above definitions, and throughout the specification and claims, lower alkyl means those radicals having one to four carbon atoms, cycloalkyl embraces those radicals having three to six carbon atoms, and halogen (or halo) represents fluoro, chloro, bromo and iodo.

Preferred compounds of the invention have the formula

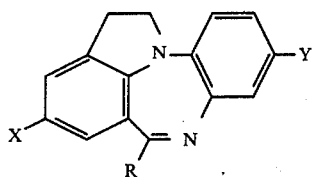

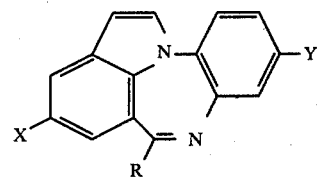

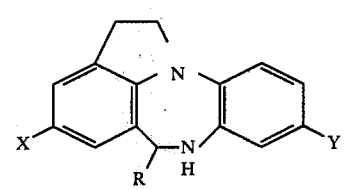

wherein X, Y and R are as defined previously.

As to the physiologically acceptable salts, those coming within the purview of this invention include pharmaceutically acceptable acid addition salts. Acids useful for preparing these acid addition salts include, inter alia, inorganic acids such as the hydrohalic acids (e.g. hydrochloric and hydrobromic acid), sulfuric acid, nitric acid, phosphoric acid and perchloric acid, and organic acids such as oxalic, malonic, succinic, maleic, fumaric, tartaric, citric, acetic, benzoic, salicylic, ascorbic, etc.

In a second embodiment, the present invention encompasses intermediate compounds of the formula

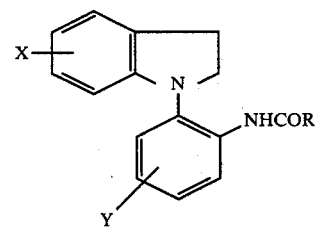

wherein X is hydrogen or halogen, and is located in the 4-, 5-, or 6- position of the indoline ring; Y is hydrogen or halogen; and R is hydrogen, loweralkyl, cycloalkyl, phenyl, halophenyl, furyl or phenylloweralkyl.

In a third embodiment, the present invention includes a cyclization process whereby intermediate compound II is reacted with POCl₃ to form final product Ia. A preferred process would ential conducting the above reaction in an inert atmosphere at from 20° C. up to the reflux temperature of the reaction mixture. Most preferred is conducting the reaction at reflux.

The compounds of the present invention may be prepared according to the following synthetic route (X, Y and R are as defined previously).

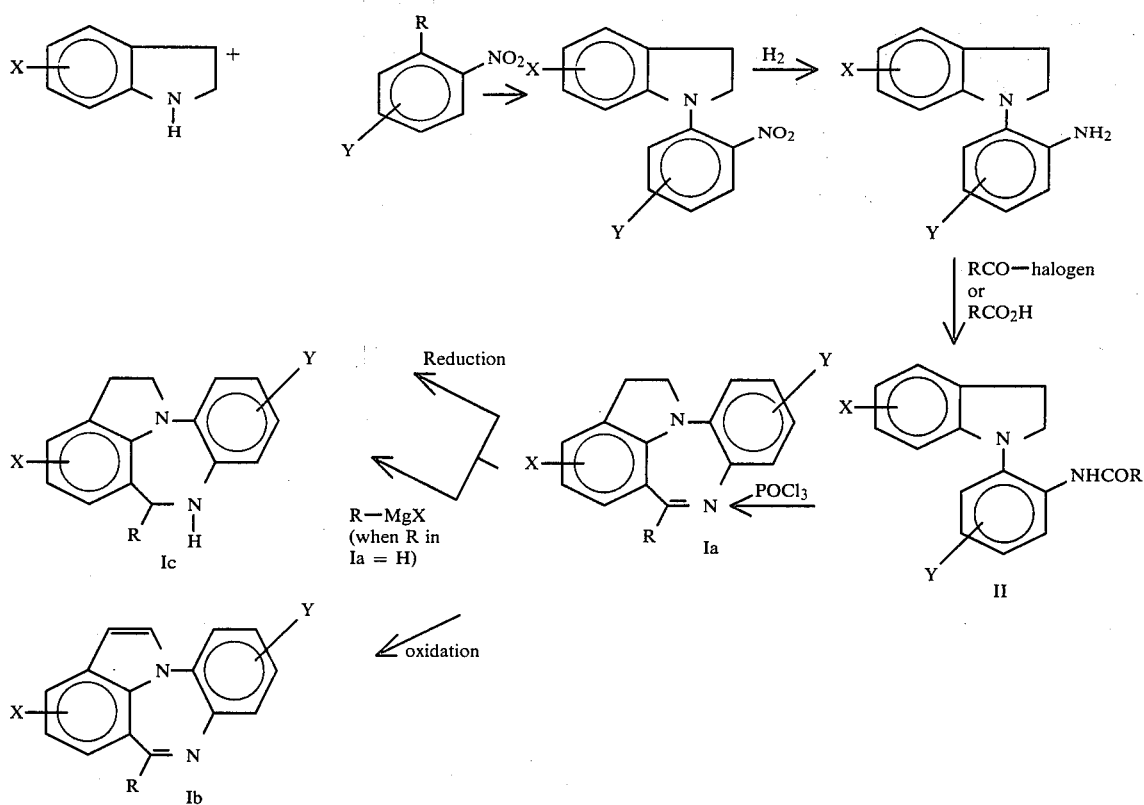

To illustrate, an X-substituted indoline wherein the X-substituent is located in the 4-, 5-, or 6-position of the indoline ring is reacted with a Y-substituted-1-fluoro-2-nitrobenzene under conventional conditions (usually T>100° C.) to yield the corresponding X-substituted-1-(Y-substituted-2-nitrophenyl)indoline. [Hereinafter, to simplify discussion the X and Y substituents will not be mentioned although they obviously will be carried forward in their respective positions as should be evident from the reaction sequence depicted above.] This product may then be reduced in a conventional manner, for example with hydrogen and a Group VIII metal catalyst, to yield the corresponding 1-(2-aminophenyl)indoline.

The amino derivative may then be converted to the corresponding amide intermediate (II) using any known technique. For example, an amide may be prepared by reacting the aminophenylindoline with an appropriate carbonyl halide, e.g., R—COCl. The carbonyl halide selected will determine the nature of the R-substituent which appears in the intermediate and final product. Intermediates wherein R is hydrogen may be advantageously prepared by treating the aminophenylindoline with formic acid or sodium methoxide in dimethylformamide (DMF). Other known amidation reactions will be readily apparent to the skilled artisan and may be employed as desired.

Final product Ia (the dihydro derivative) may be prepared by subjecting the intermediate amide (II) to a novel cyclization process of this invention. This cyclization process involves treating the amide (II) with POCL$_3$, usually in an inert atmosphere at temperatures from 20° C. up to the reflux temperature of the reaction mixture. In a most preferred embodiment, this reaction is carried out under reflux. The reaction can be carried out in the absence of a solvent, or an inert organic solvent may be used, if convenient.

Final product Ia may then be converted to final products Ib and Ic by known oxidation and reduction techniques respectively. For example, Ia may be refluxed with 2,3-dichloro-5,6-dicyano-1,4-benzoquinone (DDO) to produce Ib; and the tetrahydro derivative (Ic) may be obtained by reducing Ia with sodium borohydride or BH$_3$ in tetrahydrofuran (THF). Alternatively, the tetrahydro derivative (Ic) may be obtained by addition of a Grignard reagent to the unsaturated C$_6$-C$_7$ double bond of Ia.

The compounds of this invention are useful as anti-inflammatory agents due to their ability to suppress inflammation in mammals. This activity is demonstrated in the carrageenin induced rat paw edema anti-inflammatory assay [Proc. Soc. Exptl. Biol. Med., III, 544 (1962); J. Pharmaco. Exp. Ther., 141, 369 (1963)]. For example, under this test 100 mg/kg oral doses of 1,2-dihydro-6-methyl-indolo [1,7-ab][1,5] benzodiazepine hydrochloride and 1,2,6,7-tetrahydroindolo [1,7-ab][1,5] benzodiazepine produced an 84% and 52% inhibition of edema, respectively.

The compounds of the present invention are also useful as analgesic agents due to their ability to alleviate pain in mammals as demonstrated in the 2-phenyl-1,4-benzoquinone-induced writhing test in mice, a standard assay for analgesia [Proc. Soc. Exptl. Biol. Med., 95, 729 (1957)]. Thus, for instance, a 25 mg/kg subcutaneous dose of 1,2-dihydro-6-(2-phenylethyl)-indolo-[1,7-ab][1,5] benzodiazepine hydrochloride exhibits a 63% inhibition of writhing.

These compounds ae useful as any of the above categories of pharmaceutical agents when administered in an amount ranging from about 1 to 200 mg per Kg of body weight per day. In addition to their pharmaceutical activity, these compounds are desirable as intermediates for other pharmacologically active compounds. For example, the compounds depicted by Formula I may be used as starting materials in the synthesis of the anti-depressant agents disclosed by Glamkowski et al. in concurrently filed U.S. patent application Ser. No. 956,903, entitled "SUBSTITUTED 1,2,6,7-TETRAHYDROINDOLO [1,7-ab][1,5] BENZODIAZEPINES."

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose; a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain in addition to the active compounds, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For the purpose of topical application, the compounds of this invention may be incorporated into a solution, suspension, ointment, cream or salve. These preparations should contain at least 0.01% of the active compound but may be varied to be between 0.05 and about 20% of the weight thereof. The amount of active compound in such compositions is such that a suitable dosage will be obtained. Preferred compositions for the treatment of dermal inflammations are those containing between 0.1 and 10% of the active compound.

The topical compositions may also include the following components: water, fixed oils, polyethylene glycols, glycerol, petroleum, stearic acid, beeswax, other synthetic solvents or mixtures thereof; antibacterial agents such as benzyl alcohol or methyl paraben; antioxidants such as $\alpha$-toco-pherol acetate; chelating agents such as ethylenediaminetetraacetic acid; buffers such as acetates, citrates or phosphates; emulsifying agents such as polyoxyethylene monooleate and coloring materials and adjuvants such as ferric oxide or talc. The topical preparations can be enclosed in tubes, bottles or jars made of metal, glass or plastic.

This invention is further illustrated by the following examples.

EXAMPLE 1

1-(2-Nitrophenyl)indoline 11.0 g (0.10 mole) of indoline and 28.2 g of 1-fluoro-2-nitrobenzene are combined and the resultant solution is stirred and heated to 120° C. and kept at that temperature 18 hours. The reaction mixture is then cooled to room temperature and partitioned between chloroform and water. The chloroform layer is separated, washed with water, dried and concentrated in vacuum. The residue is dissolved in isopropylether from which 1-(2-nitrophenyl)indoline, m.p. 62°–64° C., precipitates on standing.

EXAMPLE 2

5-Chloro-1-(2-Nitrophenyl)indoline

A solution of 32.3 g of 1-fluoro-2-nitrobenzene and 92.2 g of 5-chloroindoline are stirred at 120° C. under $N_2$ overnight (20 hours). The mixture is cooled, and stirred vigorously in a two phase chloroform and water system. The undissolved material is filtered off and the organic phase is then separated, washed with 3 N—HCl, water, dried over $Na_2SO_4$, and concentrated to an oil which is dried further in vacuo at 90° C. This is taken up in isopropyl ether and refrigerated overnight to provide 5-chloro-1-(2-nitrophenyl)indoline, m.p. 85°–89° C.

Analysis: Calculated for $C_{14}H_{11}ClN_2O_2$: 61.21%C, 4.04%H, 10.20%N, 12.91%Cl; Found: 61.10%C, 4.13%H, 10.19%N, 13.16%Cl.

EXAMPLE 3

1-(2-Nitro-4-trifluoromethylphenyl)indoline

An initial solution of 22.6 g of 4-chloro-3-nitrobenzotrifluoride and 29.8 g of indoline in 500 ml of xylene is stirred and refluxed under $N_2$ for 18 hours. The indoline HCl salt which separates is filtered off, and the xylene filtrate is washed with water, with 3 N HCl, with 3 N—NaOH, and finally again with water, dried over $MgSO_4$, and concentrated to an oil on a rotovac at 60° C., first at aspirator pressure, then in vacuo. This oil is taken up in 100 ml hexane and allowed to crystallize 18 hours to yield 1-(2-nitro-4-trifluoromethylphenyl)indoline, m.p. 89°–92° C.

Analysis: Calculated for $C_{15}H_{11}F_3N_2O_2$: 58.43%C, 3.60%H, 9.09%N; Found: 57.98%C, 3.58%H, 9.18%N.

EXAMPLE 4

1-(2-Aminophenyl)indoline hydrochloride

A solution of 24.0 g of 1-(2-nitrophenyl)indoline of Example 1 in 400 ml ethanol and 40 ml benzene is shaken with 2.5 g of 5% Pd on C at 60 psi of $H_2$ until the theoretical amount of $H_2$ is taken up (1.5 hours). The mixture is filtered and the solvent removed at 50° C. to leave the free base as an oil. This is dissolved in 150 ml of ether, cooled to 0° C., and treated with gaseous HCl to precipitate the product as the hydrochloride salt. The solid is filtered, washed with ether, and dried to afford 1-(2-aminophenyl)indoline hydrochloride, m.p. 235°–240° C. dec.

Analysis: Calculated for $C_{14}H_{14}N_2 \cdot HCl$: 68.15%C, 6.13%H, 11.35%Cl; Found: 67.93%C, 6.04%H, 11.35%Cl.

EXAMPLE 5

1-(2-Aminophenyl)-5-chloroindoline hydrochloride

A mixture of 13.7 g of 5-chloro-1-(2-nitrophenyl)indoline and 0.25 g of 1% Pt on C in 250 ml absolute ethanol is shaken at 50 psi of $H_2$ until the theoretical amount of $H_2$ is taken up. The mixture is filtered and the solvent removed at 50° C. to leave the product base as an oil. This is dissolved in 200 ml of ether, cooled to 0° C., and treated with gaseous HCl to precipitate 1-(2-aminophenyl)-5-chloroindoline hydrochloride, m.p. 235°–238° C. dec.

Analysis: Calculated for $C_{14}H_{13}ClN_2 \cdot HCl$: 59.80%C, 5.02%H, 9.96%N; Found: 59.88%C, 5.15%H, 9.98%N.

EXAMPLE 6

1-(2-Amino-4-trifluoromethylphenyl)indoline hydrochloride

A mixture of 15.4 g of 1-(2-nitro-4-trifluoromethylphenyl)indoline, 1.5 g of 5% Pd on carbon and 250 ml absolute ethanol is shaken at an initial pressure of 60 psi of $H_2$ until the theoretical amount of $H_2$ is taken up. After filtration of catalyst, the solution is concentrated to an oil which sets to a waxy crystalline solid. This is dissolved in 100 ml of anhydrous ether, cooled to 0° C., and gaseous HCl is bubbled into the stirred mixture until saturated. The HCl salt of the product base is filtered, washed repeatedly with ether, and dried to give 1-(2-amino-4-trifluoromethylphenyl)indoline hydrochloride, m.p. 194°–196° C. dec.

Analysis: Calculated for $C_{15}H_{13}F_3N_2 \cdot HCl$: 57.24%C, 4.48%H, 11.26%Cl; Found: 57.15%C, 4.46%H, 11.29%Cl.

EXAMPLE 7

1-(2-Formamidophenyl)indoline

A suspension of 9.87 g of 1-(2-aminophenyl)indoline.HCl in 300 ml of toluene is treated with 4.04 g of triethylamine and the mixture is stirred for 0.5 hours. 200 ml of water is added and stirring is continued until two clear phases are produced. The layers are separated and the organic phase washed further with water, then dried over $Na_2SO_4$.

The above toluene solution containing free base is treated with 4.60 g of 97–100% formic acid, and the mixture is refluxed for 4 hours during which water is removed. The solution is then concentrated, first at aspirator pressure, then in vacuo at 100° C. bath temperature, leaving a thick oil. This is dissolved in 50 ml ether, and on cooling the solution sets solid with crystals of 1-(2-formamidophenyl)indoline, m.p. 103°–105° C.

Analysis: Calculated for $C_{15}H_{14}N_2O$: 75.61%C, 5.92%H, 11.76%N; Found: 75.73%C, 6.07%H, 11.75%N.

EXAMPLE 8

5-Chloro-1-(2-formamidophenyl)indoline

A stirred mixture, under $N_2$, of 24.3 g of 1-(2-aminophenyl)-5-chloroindoline hydrochloride, of Example 5, and 150 ml of dry dimethylformamide (DMF) is immersed in a 100° C. pre-heated oil bath. Solution occurs at 60° C. when 14.4 g of solid sodium methoxide is added in one portion. The mixture is rapidly heated to reflux and kept there for 45 minutes during which dimethylamine evolves copiously. The reaction mixture is then treated, in portions and without further heating, with 2 liters of water to precipitate the product as an oil. The water is removed by decantation. The oil is taken up in chloroform, extracted with $H_2O$, with 3N—HCl, once again with $H_2O$, dried over sodium sulfate and concentrated to a hard glass. This is dissolved in hot benzene (charcoal) to which hexane is added. The solid of 5-chloro-1-(2-formamidophenyl)indoline, m.p. 126°–129° C. is collected.

Analysis: Calculated for $C_{15}H_{13}ClN_2O$: 66.06%C, 4.80%H, 10.27%N; Found: 66.25%C, 4.92%H, 10.40%N.

EXAMPLE 9

1-(2-Formamido-4-trifluoromethylphenyl)indoline

A stirred solution of 15.7 g of 1-(2-amino-4-trifluoromethylphenyl)indoline.HCl in 75 ml of dry dimethylformamide, kept under $N_2$, is immersed in an oil bath preheated to 100° C. After 5 minutes, 8.1 g of fresh, solid sodium methoxide is added in one portion. The mixture is quickly (15 minutes) brought to reflux, and kept at reflux an additional 45 minutes. The heating bath is then removed and when the internal temperature falls to 100° C., 300 ml of water is added in portions, with vigorous stirring. The product separates first as an oil which then solidifies. This material is filtered, washed with $H_2O$, with alcohol, and dried to afford 1-(2-formamido-4-trifluoromethylphenyl)indoline, m.p. 135°–357° C.

Analysis: Calculated for $C_{16}H_{13}F_3N_2O$: 62.74%C, 4.28%H, 9.15%N; Found: 63.01%C, 4.40%H, 9.32%N.

EXAMPLE 10

1-(2-Acetamidophenyl)indoline

A stirred slurry, under $N_2$, of 9.96 g of 1-(2-aminophenyl)indoline.HCl and 300 ml of dry acetone is treated with 10.1 g of triethylamine over a 10 minute period. After cooling to 0°–5° C., 4.70 g of acetyl chloride is added dropwise over 0.5 hour. The mixture is stirred 18 hours at ambient temperature, then filtered. The filtrate is diluted with 100 ml of water and concentrated. When all the acetone is removed, the residue is filtered off, washed well with water, and dried to afford 1-(2-acetamidophenyl)indoline, m.p. 125°–128° C.

Analysis: Calculated for $C_{16}H_{16}N_2O$: 76.16%C, 6.39%H, 11.10%N; Found: 76.10%C, 6.31%H, 11.15%N.

EXAMPLE 11

1-(2-Acetamidophenyl)-5-chloroindoline 24.6 ml (0.346 mole) of acetyl chloride is added dropwise over 30 minutes to a rapidly stirred, ice cold solution of 60.6 g 1-(2-aminophenyl)-5-chorindoline and 48.8 ml triethylamine in 500 ml $CH_2Cl_2$. After stirring 5 hours at room temperature, the resulting mixture is washed with water, 10% NaOH, water and brine. The solution is dried ($MgSO_4$) and concentrated to give 1-(2-acetamidophenyl)-5-chloroindoline, m.p. 136°–138° C.

Analysis: Calculated for $C_{16}H_{15}ClN_2O$: 67.02%C, 5.27%H, 12.36%Cl, 9.77%N; Found: 66.94%C, 5.30%H, 12.47%Cl, 9.75%N.

EXAMPLE 12

1-(2-Acetamido-4-trifluoromethylphenyl)indoline

To a stirred mixture, under $N_2$, of 6.30 g of 1-(2-amino-4-trifluoromethylphenyl)indoline hydrochloride in 100 ml of dry methylene chloride is added 4.04 g of triethylamine. The mixture is then cooled to 0°–5°, and kept at that temperature while a solution of 1.57 g of acetyl chloride in 25 ml of $CH_2Cl_2$ is added dropwise over 1 hour. After stirring at room temperature overnight, water is added to dissolve the precipitated $(C_2H_5)_3N.HCl$ salt, and the layers are separated. The organic phase is washed further with 3N—HCl, 3N—NaOH, with $H_2O$ and dried over $Na_2SO_4$. The solvent is removed to yield 1-(2-acetamido-4-trifluoromethylphenyl)indoline, m.p. 153°–155° C.

Analysis: Calculated for $C_{17}H_{15}F_3N_2O$: 63.75%C, 4.72%H, 8.75%N; Found: 63.75%C, 4.71%H, 8.89%N.

EXAMPLE 13

1-[2-(N-Phenylacetyl)aminophenyl]indoline

A stirred slurry, under $N_2$, of 24.7 g of 1-(2-aminophenyl)indolinehydrochloride and 250 ml of dry methylene chloride is treated with 24.2 g of triethylamine over a 10 minute period. After cooling to 0°–5° C., a solution of 18.6 g of phenylacetyl chloride in 50 ml of $CH_2Cl_2$ is added dropwise over 1.0 hour at such a rate as to keep the reaction temperature below 5° C. When the addition is complete, the mixture is stirred at ambient temperature for 6 hours. Water is then added to dissolve the salts; the organic phase is washed with solutions of HCL, NaOH, $H_2O$, dried over $Na_2SO_4$, and concentrated on a rotary evaporator first at aspirator pressure, then in high vacuum, finally at a bath temperature of 100° to leave an oil. This oil is dissolved in 100 ml di-isopropyl ether, filtered, and allowed to stand several days. Crystals of 1-[2-(N-phenylacetyl)aminophenyl]indoline, m.p. 67°–70° C., are collected.

Analysis: Calculated for $C_{22}H_{20}N_2O$: 80.46%C, 6.14%H, 8.53%N; Found: 80.79%C, 6.58%H, 8.55%N.

EXAMPLE 14

1-[2-(3-phenyl-1-oxopropyl)aminophenyl]indoline

To a slurry of 1-(2-aminophenyl)indoline hydrochloride (24.76 g) in $CH_2Cl_2$ (200 ml) under $N_2$ at 0° C. is added 2.4 equivalents $Et_3N$ (34 ml) in $CH_2Cl_2$ (35 ml). After 45 minutes, a solution of dihydrocinnamoyl chloride (14.7 ml, 1 equivalent) in $CH_2Cl_2$ (22 ml) is added. The solution is permitted to warm to room temperature and stirred overnight.

The product is poured into water (500 ml); the aqueous layer is extracted with $CH_2Cl_2$ and the combined organic portions are washed with $H_2O$, dried ($Na_2SO_4$), filtered, and concentrated to an oil.

200 ml of petroleum ether are added to this oil and upon standing over 3 days 1-[2-(3-phenyl-1-oxopropyl)aminophenyl]indoline, m.p. 74.5°–77° C., precipitates out.

Analysis: Calculated for $C_{23}H_{22}N_2O$: 80.67%C, 6.48%H, 8.18%N; Found: 80.78%C, 6.52%H, 8.28%N.

EXAMPLE 15

1-[2-(Cyclopropylcarbonyl)aminophenyl]indoline 49.34 g of 1-(2-aminophenyl)indoline hydrochloride in 400 ml $CH_2Cl_2$ under $N_2$ at 0° C. is treated dropwise with a solution of triethylamine (62 ml, 2.2 equivalent) in $CH_2Cl_2$ (100 ml). The resulting slurry is then treated dropwise (0° C.) with a solution of cyclopropanecarbonyl chloride (18.4 ml, 0.20 mole) in $CH_2Cl_2$ (60 ml). The product is permitted to warm to room temperature and then poured into water.

The organic layer is washed with 4N HCl, 2.5N NaOH, water, dried ($Na_2SO_4$), filtered and concentrated to yield 1-[2-(cyclopropylcarbonyl)aminophenyl]indoline, m.p. 83°–85° C.

Analysis: Calculated for $C_{18}H_{18}N_2O$: 77.67%C, 6.52%H, 10.06%N; Found: 77.85%C, 6.42%H, 10.09%N.

EXAMPLE 16

1-[2-(cyclobutylcarbonyl)aminophenyl]indoline

A slurry of 1-(2-aminophenyl)indoline hydrochloride (41.44 g) in $CH_2Cl_2$ (400 ml) under $N_2$ at 0° C. is treated dropwise with a solution of triethylamine (2.2 equivalents) in $CH_2Cl_2$ (80 ml) and then with a solution of cyclobutylcarbonyl chloride (20 g) in $CH_2Cl_2$ (50 ml). After warming to room temperature, the product is poured into water (300 ml). The organic layer is washed with 4 N HCl, 2.5 N NaOH, water, dried ($Na_2SO_4$), filtered, and concentrated to yield 1-[2-(cyclobutylcarbonyl)aminophenyl]indoline, m.p. 81°–83.5° C.

Analysis: Calculated for $C_{19}H_{20}N_2O$: 78.05%C, 6.90%H, 9.58%N; Found: 78.10%C, 6.90%H, 9.36%N.

EXAMPLE 17

1-[2-(Cyclohexylcarbonyl)aminophenyl]indoline

A slurry of 1-(2-aminophenyl)indoline hydrochloride (24.67 g) in $CH_2Cl_2$ (200 ml) under $N_2$ at 0° C. is treated dropwise with a solution of triethylamine (2.4 equivalent) in CH$_2$Cl$_2$ (50 ml) and then with a solution of cyclohexanecarbonyl chloride (16.4 g) in CH$_2$Cl$_2$ (32 ml). After stirring for 2 hours at room temperature, the product is poured into water and the aqueous layer is extracted with CH$_2$Cl$_2$. The combined organic portions are washed with water, brine, dried (Na$_2$SO$_4$), filtered and concentrated to afford an oil.

The oil is dissolved in hot hexane-ether and the solution is allowed to stand for about three days to yield 1-[2-(cyclohexylcarbonyl)aminophenyl]indoline, m.p. 87°–89° C.;

Analysis: Calculated for C$_{21}$H$_{24}$N$_2$O: 78.72%C, 7.55%H, 8.74%N; Found: 78.67%C, 7.45%H, 8.63%N.

EXAMPLE 18

1-(2-Benzamidophenyl)indoline

A stirred mixture, under N$_2$, of 24.6 g of 1-(2-aminophenyl)indoline hydrochloride in 225 ml of dry CH$_2$Cl$_2$ is treated with 20.2 g of triethylamine over 10 minutes. The mixture is cooled to 0°–5° C., and kept at that temperature while a solution of 14.1 g of benzoyl chloride and 25 ml of CH$_2$Cl$_2$ is added dropwise over 1.0 hour. After stirring at room temperature overnight, H$_2$O was added and the layers are separated. The organic phase is washed further with H$_2$O, 3 N—HCl, 3 N—NaOH, again with H$_2$O, and dried. The solvent is removed to leave an oil which crystallizes on standing to yield 1-(2-benzamidophenyl)indoline, m.p. 73°–76° C.

Analysis: Calculated for C$_{21}$H$_{18}$N$_2$O: 80.23%C, 5.77%H, 8.91%N; Found: 80.15%C, 5.80%H, 8.91%N.

EXAMPLE 19

1-[2-(2-Fluorobenzamido)phenyl]indoline

A stirred mixture, under N$_2$, of 9.86 g of 1-(2-aminophenyl)indoline hydrochloride and 100 ml of dry methylene chloride is treated with 8.09 g of triethylamine. The mixture is cooled to 0°–5° C., and a solution of 6.34 g of o-fluorobenzoyl chloride in 25 ml of CH$_2$Cl$_2$ is added over 1 hour at such a rate as to keep the temperature below 5° C. The mixture is then stirred overnight at ambient temperature. Water is added, the organic layer is separated, washed with 3 N—HCl, with 3 N—NaOH, with H$_2$O, dried and concentrated to a crystalline solid of 1-[2-(2-fluorobenzamido)phenyl]indoline, m.p. 139°–141° C.

Analysis: Calculated for C$_{21}$H$_{17}$FN$_2$O: 75.89%C, 5.16%H, 8.43%N; Found: 75.62%C, 5.14%H, 8.51%N.

EXAMPLE 20

1-(2-Benzamidophenyl)-5-chloroindoline

A solution of 16.5 ml (0.143 mole) benzoyl chloride in 20 ml CH$_2$Cl$_2$ is added dropwise over 40 minutes to an ice cold rapidly stirred solution of 20.1 ml (0.143 mole) triethylamine and 31.71 g of 1-(2-aminophenyl)-5-chloroindoline hydrochloride (as the free base) in 250 ml CH$_2$Cl$_2$ under N$_2$. The reaction mixture is permitted to warm to room temperature, stand overnight, and then washed with water, 5% NaOH, water, brine, dried over MgSO$_4$ and concentrated thus giving crude amide as an oil.

The oil is chromatographed on silica gel using ether-hexane to yield 1-(2-benzamidophenyl)-5-chloroindoline, m.p. 44°–46° C.

Analysis: Calculated for C$_{21}$H$_{17}$ClN$_2$O: 72.31%C, 4.91%H, 8.03%N, 10.16%Cl; Found: 72.04%C, 4.95%H, 7.88%N, 10.34%Cl.

EXAMPLE 21

1-(2-Benzamido-4-trifluoromethylphenyl)indoline

A stirred mixture, under N$_2$, of 12.6 g of 1-(2-amino-4-trifluoromethylphenyl)indoline hydrochloride in 150 ml of dry CH$_2$Cl$_2$ is treated with 8.09 g of triethylamine. The mixture is cooled to 0°–5° C., and kept at that temperature while a solution of 5.62 g of benzoyl chloride and 25 ml of CH$_2$Cl$_2$ is added dropwise over 1.0 hour. After stirring at room temperature overnight, water is added to dissolve (C$_2$H$_5$)$_3$N.HCl and the layers are separated. The organic phase is extracted further with water, 3 N—HCl, 3 N—NaOH, water again and dried over N$_2$SO$_4$. The solvent is removed leaving an oil which, when digested with ether, becomes a crystalline mass. After cooling, 1-(2-benzamido-4-trifluoromethylphenyl)indoline is obtained having m.p. 114°–119° C.

Analysis: Calculated for C$_{22}$H$_{17}$F$_3$N$_2$O: 69.10%C, 4.48%H, 7.33%N; Found: 68.74%C, 4.40%H, 7.25%N.

EXAMPLE 22

1-[2'-(2-fluorobenzoylamino)-4'-trifluoromethylphenyl]indoline

To a stirred mixture, under N$_2$, of 10.2 g of 1-(2-amino-4-trifluoromethylphenyl)indoline hydrochloride in 100 ml of dry methylene chloride is added 7.08 g of triethylamine. The mixture is cooled to 0°–5° C., and kept at that temperature while a solution of 5.71 g of o-fluorobenzoyl chloride in 50 ml of dry methylene chloride is added dropwise over 1 hour. After stirring at room temperature overnight, water is added to dissolve the precipitated (C$_2$H$_5$)$_3$N.HCl salt, and the layers are separated. The organic phase is washed further with 3 N—HCl, 3 N—NaOH, with water and dried over sodium sulfate. The solvent is removed leaving an oil which is dissolved in 25 ml of ethanol and sets solid on cooling. The crystals are collected, washed with ethanol, and dried to afford 1-[2'-(2-fluorobenzoylamino)-4'-trifluoromethylphenyl]indoline, m.p. 127°–130° C.

Analysis: Calculated for C$_{22}$H$_{16}$F$_4$N$_2$O: 66.00%C, 4.03%H, 7.00%N; Found: 65.85%C, 4.02%H, 7.02%N.

EXAMPLE 23

1-(2-Furoylaminophenyl)indoline

A slurry of 1-(2-aminophenyl)indoline hydrochloride of Example 4 (24.67 g) in CH$_2$Cl$_2$ (200 ml) at 0° C. is treated dropwise with a solution of triethylamine (0.24 mole) in CH$_2$Cl$_2$ (50 ml). A solution of furoylchloride (14.5 g) in CH$_2$Cl$_2$ (33 ml) is then added at 0° C. and the product is permitted to warm at room temperature and stirred for 2 hours. The mixture is poured into water and the aqueous layer is extracted with CH$_2$Cl$_2$. The combined organic portions are washed with water, brine, dried (Na$_2$SO$_4$), filtered, and concentrated to afford an oil.

The oil is dissolved in hot chloroform-hexane and stored in a refrigerator for about 72 hours to yield 1-(2-furoylaminophenyl)indoline, m.p. 99°–101.5° C.

Analysis: Calculated for C$_{19}$H$_{16}$N$_2$O$_2$: 74.98%C, 5.30%H, 9.32%N; Found: 74.76%C, 5.39%H, 9.35%N.

EXAMPLE 24

1,2-Dihydroindolo[1,7-ab][1,5]benzodiazepine hydrochloride

A mixture of 14.0 g of 1-(2-formamidophenyl)indoline and 50 ml of fresh phosphorus oxychloride are stirred and heated under N$_2$. The mixture is refluxed 4.0 hours, then left at room temperature 18 hours. Excess POCl$_3$ is then removed, leaving a solid which is triturated and boiled with absolute ethanol. The mixture is stirred 1 hour to homogenize the fine solid, then filtered, washed with ethanol, and dried to afford 1,2-dihydroindolo[1,7-ab][1,5]benzodiazepine hydrochloride, m.p. 228°-230° C. dec.

Analysis: Calculated for C$_{15}$H$_{12}$N$_2$.HCl: 70.18%C, 5.10%H, 10.91%N; Found: 70.16%C, 5.18%H, 10.84%N.

EXAMPLE 25
4-Chloro-1,2-dihydroindolo[1,7-ab][1,5]benzodiazepine hydrochloride A mixture of 9.40 g of 5-chloro-1-(2-formamidophenyl)indoline and 45 ml of phosphorus oxychloride is stirred under nitrogen. After a short time, a purple solution results. While heating this to reflux, a solid precipitates at 60° C. During the early stages of a 6 hour reflux period a solution is obtained again followed by heavy HCl (g) evolution and separation of a solid. The mixture is cooled and 45 ml of hexane is added to give a finely divided purple solid. This is filtered, washed repeatedly with hexane and dried. For purification, the solid is slurried in absolute ethanol, and tri-n-butylamine is added until a color change, indicating liberation of the free base of the product. The mixture is warmed to produce a solution, and the base allowed to crystallize at 0° C. The base is collected, washed with ethanol and dried. To reform the HCl salt, the base is dissolved in 15 ml of dimethylformamide without heating, and to the solution is added 35 ml of ethanol saturated with HCl gas. The product of 4-chloro-1,2-dihydroindolo[1,7-ab][1,5]benzodiazepine hydrochloride crystallizes rapidly in the form of needles with m.p. 231°-233° C. dec.

Analysis: Calculated for C$_{15}$H$_{11}$ClN$_2$.HCl: 61.87%C, 4.15%H, 9.62%N; Found: 61.73%C, 4.08%H, 9.47%N.

EXAMPLE 26
1,2-Dihydro-6-methyl-indolo[1,7-ab][1,5]benzodiazepine .HCl

A mixture of 17.0 g of 1-(2-acetamidophenyl)indoline of Example 10 and 40 ml of fresh phosphorus oxychloride is stirred and heated under N$_2$ at reflux for 4 hours. After the reflux period, the solution is cooled and the excess POCl$_3$ is removed leaving a solid which is triturated and boiled with absolute ethanol. On cooling, the crystalline product is filtered, washed and dried resulting in 1,2-dihydro-6-methyl-indolo[1,7-ab][1,5]benzodiazepine.HCl, m.p. 248°-249° C. dec.

Analysis: Calculated for C$_{16}$H$_{14}$N$_2$.HCl: 70.98%C, 5.58%H, 13.09%Cl; Found: 70.89%C, 5.54%H, 12.92%Cl.

EXAMPLE 27
4-Chloro-1,2-dihydro-6-methylindolo[1,7-ab][1,5]benzodiazepine hydrochloride A mixture of 286.8 g of 1-(2-acetamidophenyl)-5-chloro-indoline and 1250 ml POCl$_3$ is stirred for 1 hour at room temperature and then slowly heated to reflux. After 20 hours, the resulting solution is permitted to cool and the POCl$_3$ is distilled off at reduced pressure. The residue is then cautiously triturated with absolute ethanol (spontaneous vigorous boiling) and then boiled for 0.5 hour. After cooling to room temperature, the resulting solid is filtered, washed with ethanol and then with ether and dried at 60° C. under vacuum to give 4-chloro-1,2-dihydro-6-methylindolo[1,7-ab][1,5]benzodiazepine hydrochloride, m.p. 251°-254° C. dec.

Analysis: Calculated for C$_{16}$H$_{13}$ClN$_2$.HCl: 62.97%C, 4.62%H, 9.18%N, 23.23%Cl; Found: 63.26%C, 4.54%H, 9.18%N, 22.65%Cl.

EXAMPLE 28
1,2-Dihydro-6-methyl-9-trifluoromethylindolo[1,7-ab][1,5]benzodiazepine hydrochloride To 40 ml of fresh phosphorus oxychloride, under N$_2$ and with stirring, is added 8.0 g of 1-(2-acetamido-4-trifluoromethylphenyl)indoline of Example 12. The resultant solution is heated at reflux overnight. After cooling to room temperature, the excess POCl$_3$ is removed to leave a glassy foam. This foam is dissolved in boiling absolute ethanol which separates 1,2-dihydro-6-methyl-9-trifluoromethylindolo[1,7-ab][1,5]benzodiazepine hydrochloride, m.p. 240°-242° C. dec.

Analysis: Calculated for C$_{17}$H$_{13}$F$_3$N$_2$.HCl: 60.28%C, 4.17%H, 8.27%N; Found: 60.13%C, 4.20%H, 8.33%N.

EXAMPLE 29
6-Benzyl-1,2-dihydroindolo[1,7-ab][1,5]benzodiazepine hydrochloride A stirred mixture of 4.93 g of 1-[2-(N-phenylacetyl)-aminophenyl]indoline and 20 ml of phosphorus oxychloride is refluxed under N$_2$ for 18 hours. The excess reagent is then removed, and the resulting residue is boiled and triturated with absolute ethanol. After prolonged standing crystals form which are filtered, washed with ethanol and dried to yield 6-benzyl-1,2-dihydroindolo[1,7-ab][1,5]benzodiazepine hydrochloride, m.p. 220°-225° C. dec.

Analysis: Calculated for C$_{22}$H$_{18}$N$_2$.HCl: 76.18%C, 5.52%H, 8.08%N; Found: 76.22%C, 5.49%H, 8.16%N.

EXAMPLE 30
1,2-Dihydro-6-(2-phenylethyl)-indolo[1,7-ab][1,5]benzodiazepine hydrochloride A rapidly stirred solution of 52.65 g of 1-[2-(3-phenyl-1-oxo-propyl)aminophenyl]indoline in 200 ml POCl$_3$ under N$_2$ is slowly brought to 105°-115° C. After 9.5 hours, the mixture is permitted to cool to room temperature for over 48 hours. The excess POCl$_3$ is distilled at aspirator pressure (bath temperature 55°-60° C.) to yield a solid which is triturated with hexane, filtered, washed with additional hexane, and dried at room temperature under high vacuum to yield 1,2-dihydro-6-(2-phenylethyl)-indolo[1,7-ab][1,5]benzodiazepine hydrochloride, m.p. 181.5°-183.0° C.

Analysis: Calculated for C$_{23}$H$_{20}$N$_2$.HCl: 76.55%C, 5.86%H, 7.76%N; Found: 76.57%C, 5.90%H, 7.85N.

EXAMPLE 31
6-Cyclohexyl-1,2-dihydroindolo-[1,7-ab][1,5]benzodiazepine

A solution of 1-[2-(cyclohexylcarbonyl)aminophenyl]indoline (12.10 g) in POCl$_3$ (50 ml) under N$_2$ is slowly brought to reflux and maintained at this temperature for 4 hours. The solvent is distilled in vacuo to afford an oil (the HCl salt). The free base is liberated by treatment of an ethanolic solution of the crude HCl salt with tri-n-butyl-amine. The resulting solution is partitioned between water and ether and the aqueous layer is extracted further with ether. The combined organic layers are washed with water and brine, dried ($K_2CO_3$), and concentrated to give an oil. Recrystallization from hot ethanol-water affords a solid of 6-cyclohexyl-1,2-dihydroindolo-[1,7-ab][1,5]benzodiazepine, m.p.: 104°–106.5° C.

Analysis: Calculated for $C_{21}H_{22}N_2$: 83.40%C, 7.33%H, 9.26%N; Found: 83.30%C, 7.31%H, 9.19%N.

EXAMPLE 32

1,2-Dihydro-6-phenylindolo[1,7-ab][1,5]benzodiazepine

A solution of 15.0 g of 1-(2-benzamidophenyl)indoline of Example 19, and 45 ml of phosphorus oxychloride is refluxed under $N_2$ for 4 hours and then the excess reagent is removed to leave a syrup which is dissolved in absolute ethanol, boiled one hour, then concentrated again to a dark purple syrup which eventually solidifies afftter prolonged standing. This material is slurried in absolute ethanol, and treated dropwise with enough $Bu_3N$ to change the color from purple to orange-brown, whereupon the product base crystallizes voluminously. After refrigeration overnight, the resultant orange-brown flakes are collected, washed with ethanol and hexane, and dried to afford 1,2-dihydro-6-phenylindolo[1,7-ab][1,5]benzodiazepine, m.p.141°–143° C.

Analysis: Calculated for $C_{21}H_{16}N_2$: 86.10%C, 5.44%H; Found: 84.99%C, 5.50%H.

EXAMPLE 33

1,2-Dihydro-6-(o-fluorophenyl)indolo[1,7-ab][1,5]benzodiazepine Hydrochloride

To 11.5 g of 1-[2-(o-fluorobenzamido)-phenyl]indoline is added 50 ml of fresh phosphorus oxychloride. After stirring under $N_2$ for 15 minutes, a pale green solution results. Tis is refluxed overnight (22 hours) to produce a purple solution. The excess $POCl_3$ is removed by distillation leaving a solid. The solid is triturated and boiled with absolute ethanol, then stirred at room temperature for 2 hours to homogenize the tiny crystals. Filtration, washing with ethanol, and drying afford a solid having m.p. 235° dec. For purification, this is slurried in absolute ethanol and tri-n-butyl amine is added until the blue-black mixture becomes orange-brown and the free base of the product crystallizes in the form of pure orange-brown flakes, m.p. 128°–130° C.

Analysis: Calculated for $C_{21}H_{15}N_2F$: 80.24%C, 4.81%H, 9.91%N; Found: 79.92%C, 4.83%H, 8.94%N.

The base is slurried with 30 ml of ethanol and ethanolic HCl is added until the color turns blue followed by rapid crystallization of the product salt. This is collected, washed once with a little ethanol and dried to furnish 1,2-dihydro-6-(o-fluorophenyl)indolo[1,7-ab][1,5]benzodiazepine hydrochloride, m.p. 235° C. dec.

Analysis: Calculated for $C_{21}H_{15}FN_2 \cdot HCl$: 71.89%C, 4.60%H, 7.98%N; Found: 71.67%C, 4.63%H, 7.76%N.

EXAMPLE 34

4-Chloro-1,2-dihydro-6-phenylindolo[1,7-ab][1,5]benzodiazepine hydrochloride

An ice cold solution of 43.48 g of 1-(2-benzamidophenyl)-5-chloroindoline in 150 ml $CH_2Cl_2$ is treated dropwise over 80 minutes with 215 ml $POCl_3$. At the end of the addition, the reaction mixture is permitted to warm to room temperature and the solvent ($CH_2Cl_2$) is distilled off at ambient pressure. The resulting $POCl_3$ solution is heated at reflux for 5 hours and then permitted to cool under $N_2$ to room temperature and stand overnight. The $POCl_3$ is distilled off at aspirator pressure. The resulting crude salt is treated cautiously with absolute ethanol and then boiled. The product is filtered, washed with 1:1 ethanol-ether, then with dry ether and is suction dried. Recrystallization from hot ethanol affords 4-chloro-1,2-dihydro-6-phenylindolo[1,7-ab][1,5]benzodiazepine hydrochloride, m.p. 231° C. dec.

Analysis: Calculated for $C_{21}H_{15}ClN_2 \cdot HCl$: 68.68%C, 4.39%H, 19.30%Cl, 7.63%N; Found: 68.41%C, 4.44%H, 18.95%C, 7.57%N.

EXAMPLE 35

1,2-Dihydro-6-furylindolo[1,7-ab][1,5]benzodiazepine

Addition of 50 ml of $POCl_3$ to 11.2 g of 1-(2-furoylaminophenyl)indoline at room temperature produces a solution which is slowly brought to reflux. After 5 hours, the $POCl_3$ is distilled at aspirator pressure and then under high vacuum (0.3 mm) to afford an oil. This material is dissolved in hot absolute ethanol and permitted to stand overnight to afford the product as the HCl salt, m.p. 207°–209° C. This material is dissolved in ethanolic NaOH and water is added until a solid forms. This material is filtered, washed with water and dried in vacuo affording 1,2-dihydro-6-furylindolo[1,7-ab][1,5]benzodiazepine, m.p. 144°–146° C.

Analysis: Calculated for $C_{19}H_{16}N_2O$: 79.70%C, 4.93%H, 9.78%N; Found: 79.17%C, 5.04%H, 9.80%N.

EXAMPLE 36

6-Phenylindolo[1,7-ab][1,5]benzodiazepine

A stirred solution, under $N_2$, of 8.7 g of 1,2-dihydro-6-phenylindolo[1,7-ab][1,5]benzodiazepine in 125 ml of xylene is heated to 100° C. when 7.34 g of 2,3-dichloro-5,6-dicyano-1,4-benzoquinone (DDQ) is added in one portion. The mixture is brought to reflux and kept there for 3.0 hours. After cooling to room temperature, the liquid is filtered and the residue remaining in the flask is rinsed with xylene. The xylene filtrate is concentrated to an oil. This oil is dissolved in ethanol, and the solution is allowed to cool at 0° C. The crystals so obtained are filtered, washed with a little ethanol, then dried to yield 6-phenylindolo[1,7-ab][1,5]benzodiazepine, m.p. 128°–136° C.

Analysis: Calculated for $C_{21}H_{14}N_2$: 85.69%C, 4.79%H; Found: 85.44%C, 4.82%H.

EXAMPLE 37

1,2,6,7-Tetrahydroindolo[1,7-ab][1,5]benzodiazepine

A stirred mixture, under $N_2$, of 18.0 g of 1,2-dihydroindolo[1,7-ab][1,5]benzodiazepine hydrochloride and 100 ml of absolute ethanol is cooled to 0° C., and sodium borohydride is added in small portions and at such a rate as to minimize frothing and to keep the reaction temperature below 5° C. The addition takes about 1 hour and 3 g of $NaBH_4$ is required to discharge the initial maroon color, and another 0.5 g is added to insure complete reduction. An hour later, water is added in portions to decompose excess reagent and maximize precipitation of product. The crystalline solid is filtered, washed well with water and dried to yield 1,2,6,7-tetrahydroindolo[1,7-ab][1,5]benzodiazepine, m.p. 175°–177° C.

Analysis: Calculated for $C_{15}H_{14}N_2$: 81.05%C, 6.35%H; Found: 81.13%C, 6.41%H.

EXAMPLE 38

4-Chloro-1,2,6,7-tetrahydroindolo[1,7-ab][1,5]benzodiazepine hydrochloride

To a well stirred mixture of 7.20 g of 4-chloro-1,2-dihydroindol-[1,7-ab][1,5]benzodiazepine hydrochloride in 50 ml absolute ethanol, cooled to 0° C., is added sodium borohydride in portions until the initial purple color is discharged. The mixture is stirred 1 hour longer at 0° C. and then water is added in portions to destroy excess reagent and to maximize precipitation of the product. The latter is filtered, washed well with water and dried and then recrystallized from benzene-hexane (charcoal). The final purification is by salt formation. The product is dissolved in hot ethanol to which is added ether saturated with HCl(g) until crystals appear. After several hours, these are filtered, washed with ether and dried to afford 4-chloro-1,2,6,7-tetrahydroindolo[1,7-ab][1,5]benzodiazepine hydrochloride, m.p. 248°-251° C. dec.

Analysis: Calculated for $C_{15}H_{13}ClN_2 \cdot HCl$: 61.45%C, 4.81%H, 9.55%N; Found: 61.56%C, 5.05%H; 9.77%N.

EXAMPLE 39

6-Methyl-1,2,6,7-tetrahydroindolo[1,7-ab][1,5]benzodiazepine

A stirred mixture, under $N_2$, of 24.3 g (0.09 mole) of 1,2-dihydro-6-methylindolo[1,7-ab][1,5]benzodiazepine hydrochloride and 200 ml of absolute ethanol is cooled to 0° C. Then sodium borohydride is added in small portions and at such a rate as to minimize foaming and to maintain the reaction below 10° C. A total of 4.0 g of $NaBH_4$ is added, 3.4 g to discharge the initial purple color, 0.6 g more to insure completeness of reduction. After 2 hours more at ambient temperature, water is added in portions to decompose excess reagent and to maximize precipitation of product. The solid is collected, washed repeatedly with water, and dried to yield product with m.p. 127°-134° C. Recrystallization from 75 ml of benzene (charcoal) afforded 6-methyl-1,2,6,7-tetrahydroindolo-[1,7-ab][1,5]benzodiazepine, m.p. 134°-136° C.

Analysis: Calculated for $C_{16}H_{16}N_2$: 81.32%C, 6.82%H; Found: 81.17%C, 6.84%H.

EXAMPLE 40

6-Methyl-1,2,6,7-tetrahydroindolo[1,7-ab][1,5]benzodiazepine

To a stirred solution of 2.00 g of 1,2-dihydroindolo[1,7-ab][1,5]benzodiazepine in 40 ml of tetrahydrofuran, cooled under $N_2$ to 0° C., is added dropwise 10 ml of a 2.5 molar solution of methyl magnesium bromide in ether. The reaction mixture is refluxed for 3 hours, cooled, and treated cautiously with saturated aqueous $NH_4OH$ solution. The mixture is partitioned between $CH_2Cl_2$ and water. The organic phase is separated, washed once with brine, dried over $Na_2SO_4$ and concentrated to a solid of 6-methyl-1,2,6,7-tetrahydroindolo[1,7-ab][1,5]benzodiazepine, m.p. 134°-136° C.

EXAMPLE 41

4-Chloro-6-methyl-1,2,6,7-tetrahydroindolo[1,7-ab][1,5]benzodiazepine

To a well stirred mixture of 45.0 g of 4-chloro-6-methyl-1,2-dihydroindolo[1,7-ab][1,5]benzodiazepine hydrochloride, in 450 ml of absolute ethanol, cooled to 0° C. under $N_2$, is added sodium borohydride in portions until the initial purple color is discharged. The mixture is stirred 1 hour longer at 0° C., then 2 hours at room temperature. Then water is added in portions to destroy excess reagent and to maximize precipitation of product. The latter is filtered, washed well with water and dried to yield 4-chloro-6-methyl-1,2,6,7-tetrahydroindolo[1,7-ab][1,5]benzodiazepine, m.p. 167°-170° C.

Analysis: Calculated for $C_{16}H_{15}ClN_2$: 70.98%C, 5.58%H, 10.35%N; Found: 71.10%C, 5.31%H, 10.29%N.

EXAMPLE 42

6-(2-Phenylethyl)-1,2,6,7-tetrahydroindolo[1,7-ab][1,5]benzodiazepine oxalate (2:1 salt)

A rapidly stirred, ice cold solution of 24.40 g of 1,2-dihydro-6-(2-phenylethyl)-indolo[1,7-ab][1,5]benzodiazepine hydrochloride in 200 ml absolute ethanol under $N_2$ is treated portionwise with 2.93 g $NaBH_4$ at such a rate that the temperature did not rise above 10° C. After warming to 15° C. over 1.5 hours, water is added portionwise. The product is extracted with $CH_2Cl_2$ and the organic phase is washed with brine, dried over $K_2CO_3$, concentrated, and pumped under high vacuum at 70° C. affording the free base as an oil.

To a rapidly stirred solution of the free base in dry ether is added in one portion an ethereal solution of oxalic acid. The resulting fine white solid is filtered, washed with dry ether, and dried under high vacuum at 37° C. affording 6-(2-phenylethyl)-1,2,6,7-tetrahydroindolo[1,7-ab][1,5]benzodiazepine oxalate, m.p. 191.5°-193.5° C., dec.

Analysis: Calculated for $C_{23}H_{22}N_2 \cdot \frac{1}{2}C_2H_2O_4$: 77.81%C, 5.98%H, 7.56N; Found: 78.14%C, 6.08%H, 7.74%N.

EXAMPLE 43

6-Cyclohexyl-1,2,6,7-tetrahydroindolo[1,7-ab][1,5]benzodiazepine

A solution of 8.81 g of 6-cyclohexyl-1,2-dihydroindolo[1,7-ab][1,5]benzodiazepine in 50 ml dry THF is added dropwise to an ice cold solution of $BH_3$ in THF (90 ml of 1 M solution; 0.090 mole) under $N_2$. The resulting solution is refluxed for 15 minutes, cooled to 0° C., treated dropwise with 6 M HCl, and gently refluxed for 1 hour. The resulting clear solution is cooled to 0° C. and made basic with solid NaOH. The aqueous phase is extracted with ether and the combined organic layers are washed with brine, dried over $K_2CO_3$, and concentrated to give an oil. Two crystallizations from ether/heptane yield 6-cyclohexyl-1,2,6,7-tetrahydroindolo[1,7-ab][1,5]benzodiazepine, m.p. 136°-137.5° C.

Analysis: Calculated for $C_{21}H_{24}N_2$: 82.85%C, 7.95%H, 9.20%N; Found: 82.74%C, 7.98%H, 9.00%N.

EXAMPLE 44

6-Phenyl-1,2,6,7-tetrahydroindolo[1,7-ab][1,5]benzodiazepine

A stirred mixture, under $N_2$, of 23.0 g of 1,2-dihydro-6-phenylindolo[1,7-ab][1,5]benzodiazepine in 200 ml of absolute ethanol is cooled to 0°-5° C. Sodium borohydride is then added in small portions and at such a rate as to keep the reaction temperature less than 5° C., and to minimize foaming. About 3 g. are required to discharge the initial blue-purple color, and another 1 g. is added to insure complete reduction. The mixture is then stirred 1 hour at 0° C. and 1 hour at room temperature. Water is added, the product is filtered, washed repeatedly with water, and dried to give 6-phenyl-1,2,6,7-tetrahydroindolo[1,7-ab][1,5]benzodiazepine, m.p. 161°–164° C.

Analysis: Calculated for $C_{21}H_{15}N_2$: 84.53%C, 6.08%H; Found: 84.45%C, 6.00%H.

EXAMPLE 45

6-Phenyl-1,2,6,7-tetrahydroindolo[1,7-ab][1,5]benzodiazepine

A stirred mixture of 2.1 g of 1,2-dihydroindolo[1,7-ab][1,5]benzodiazepine in 16 ml of dry tetrahydrofuran is cooled under $N_2$ to 0°–5° C., then treated dropwise with 9.4 ml of a 2.8 molar solution of phenyl magnesium bromide in ether at such a rate as to keep the reaction temperature below 10° C. When the addition is complete, the reaction mixture is refluxed for 3 hours, cooled and then poured into 100 ml ice-water containing 10 ml of concentrated HCl. The resultant mixture is made alkaline with $NH_4OH$ and extracted with methylenechloride. The organic phase is separated, washed with brine, dried over $Na_2SO_4$ and concentrated to give 6-phenyl-1,2,6,7-tetrahydroindolo[1,7-ab][1,5]benzodiazepine, m.p. 161°–164° C.

EXAMPLE 46

4-Chloro-6-phenyl-1,2,6,7-tetrahydroindolo[1,7-ab][1,5]benzodiazepine 1.65 g $NaBH_4$ is added portionwise over 6 minutes to rapidly stirred ice cold slurry of 4.0 g 4-chloro-1,2-dihydro-6-phenylindolo[1,7-ab][1,5]benzodiazepine hydrochloride in 50 ml absolute ethanol under $N_2$. After 70 minutes at 0° C., water is added dropwise over 10 minutes and the reaction mixture is concentrated to leave an oil. The resulting oil is dissolved in $CHCl_3$, washed with water, brine, dried over $Na_2SO_4$, and concentrated to give 4-chloro-6-phenyl-1,2,6,7-tetrahydroindolo[1,7-ab][1,5]benzodiazepine, m.p. 192.5°–194.5° C.

Analysis: Calculated for $C_{21}H_{17}ClN_2$: 75.78%C, 5.15%H, 10.65%Cl, 8.42%N; Found: 75.80%C, 5.23%H, 10.79%Cl, 8.47%N.

EXAMPLE 47

6-Furyl-1,2,6,7-tetrahydroindolo[1,7-ab][1,5]benzodiazepine

An ice cold solution of 8.88 g of 1,2-dihydro-6-furylindolo[1,7-ab][1,5]benzodiazepine (HCl salt) in 100 ml 3:1 absolute ethanol-THF is treated portionwise with 2.5 g $NaBH_4$ added at such a rate as to minimize foaming. After stirring for 1.5 hours at 0° C., water is added dropwise and the product is partitioned in $CH_2Cl_2$-water. The aqueous phase is extracted with $CH_2Cl_2$ and the combined organic portions are washed with brine, dried over $K_2CO_3$, and concentrated to an oil which solidifies upon standing to yield 6-furyl-1,2,6,7-tetrahydroindolo[1,7-ab][1,5]benzodiazepine, m.p. 141°–144° C.

Analysis: Calculated for $C_{19}H_{16}N_2O$: 79.14%C, 5.59%H, 9.71%N; Found: 79.25%C, 5.40%H, 9.60%N.

We claim:

1. A compound of the formula

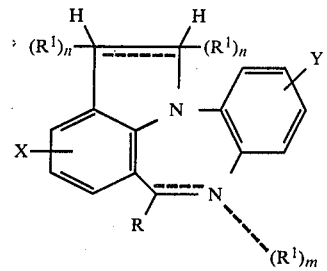

or a pharmaceutically acceptable acid addition salt thereof, wherein
X is hydrogen or halogen;
Y is hydrogen, halogen or trifluoromethyl;
R is hydrogen, lower alkyl, cycloalkyl of 3 to 6 carbon atoms, phenyl, halophenyl, furyl or phenyl-loweralkyl;
$R^1$ is hydrogen;
n and m are independently 0 or 1, but n is not 0 when m is 1, and the bonds between positions 1 and 2 and between positions 6 and 7 are respectively saturated when n and m are 1 and are unsaturated when n and ma are 0.

2. A compound or salt as in claim 1 having the formula

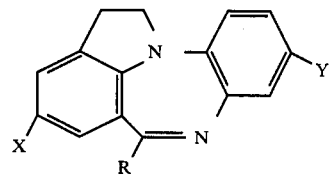

3. The compound as defined in claim 1 which is 1,2-dihydroindolo[1,7-ab][1,5]benzodiazepine or a salt thereof.

4. The compound as defined in claim 1 which is 4-chloro-1,2-dihydroindolo[1,7-ab][1,5]benzodiazepine or a salt thereof.

5. The compound as defined in claim 1 which is 1,2-dihydro-6-methylindolo[1,7-ab][1,5]benzodiazepine or a salt thereof.

6. The compound as defined in claim 1 which is 4-chloro-1,2-dihydro-6-methylindolo[1,7-ab][1,5]benzodiazepine or a salt thereof.

7. The compound as defined in claim 1 which is 1,2-dihydro-6-methyl-9-trifluoromethylindolo[1,7-ab][1,5]benzodiazepine or a salt thereof.

8. The compound as defined in claim 1 which is 6-benzyl-1,2-dihydroindolo[1,7-ab][1,5]benzodiazepine or a salt thereof.

9. The compound as defined in claim 1 which is 1,2-dihydro-6-(2-phenylethyl)-indolo[1,7-ab][1,5]benzodiazepine or a salt thereof.

10. The compound as defined in claim 1 which is 6-cyclohexyl-1,2-dihydroindolo[1,7-ab][1,5]benzodiazepine or a salt thereof.

11. The compound as defined in claim 1 which is 1,2-dihydro-6-phenylindolo[1,7-ab][1,5]benzodiazepine or a salt thereof.

12. The compound as defined in claim 1 which is 1,2-dihydro-6-(o-fluorophenyl)indolo[1,7-ab][1,5]benzodiazepine or a salt thereof.

13. The compound as defined in claim 1 which is 4-chloro-1,2-dihydro-6-phenylindolo[1,7][1,5]benzodiazepine or a salt thereof.

14. The compound as defined in claim 1 which is 1,2-dihydro-6-furylindolo[1,7-ab][1,5]benzodiazepine or a salt thereof.

15. The compound as defined in claim 1 which is 6-phenylindolo[1,7-ab][1,5]benzodiazepine or a salt thereof.

16. The compound as defined in claim 1 which is 1,2,6,7-tetrahydroindolo[1,7-ab][1,5]benzodiazepine or a salt thereof.

17. The compound as defined in claim 1 which is 4-chloro-1,2,6,7-tetrahydroindolo[1,7-ab][1,5]benzodiazepine or a salt thereof.

18. The compound as defined in claim 1 which is 6-methyl-1,2,6,7-tetrahydroindolo[1,7-ab][1,5]benzodiazepine or a salt thereof.

19. The compound as defined in claim 1 which is 4-chloro-6-methyl-1,2,6,7-tetrahydroindolo[1,7-ab][1,5]benzodiazepine or a salt thereof.

20. The compound as defined in claim 1 which is 6-(2-phenylethyl)-1,2,6,7-tetrahydroindolo[1,7-ab][1,5]benzodiazepine or a salt thereof.

21. The compound as defined in claim 1 which is 6-cyclohexyl-1,2,6,7-tetrahydroindolo[1,7-ab][1,5]benzodiazepine or a salt thereof.

22. The compound as defined in claim 1 which is 6-phenyl-1,2,6,7-tetrahydroindolo[1,7-ab][1,5]benzodiazepine or a salt thereof.

23. The compound as defined in claim 1 which is 4-chloro-6-phenyl-1,2,6,7-tetrahydroindolo[1,7-ab][1,5]benzodiazepine or a salt thereof.

24. The compound as defined in claim 1 which is 6-furyl-1,2,6,7-tetrahydroindolo[1,7-ab][1,5]benzodiazepine or a salt thereof.

25. A method of treating inflammation which comprises administering to a patient in need thereof a pharmaceutically effective amount of a compound defined in claim 1.

26. A method of treating pain which comprises administering to a patient in need thereof a pharmaceutically effective amount of a compound defined in claim 1.

27. A pharmaceutical composition which comprises between about 0.5 and about 70 percent by weight of a compound defined in claim 1 and a pharmaceutically acceptable carrier therefor.

* * * * *

UNITED STATES PATENT AND TRADEMARK OFFICE
CERTIFICATE OF CORRECTION

PATENT NO. : 4,186,199
DATED : January 29, 1980
INVENTOR(S) : Glamkowski et al.

It is certified that error appears in the above-identified patent and that said Letters Patent are hereby corrected as shown below:

Column 2, line 61, "ential" should be --entail--;

Column 3, line 1, in the second structural formula, "R" should be --F--;

Column 15, line 17, "affter" should be --after--;

Column 15, line 34, "Tis" should be --This--;

Column 16, line 1, "$POCl_3$is" should be --$POCl_3$ is--;

Column 18, line 35, "7.56N" should be --7.56%N--; and

Column 20, line 26, "ma" should be --m--.

Signed and Sealed this

First Day of July 1980

[SEAL]

Attest:

Attesting Officer

SIDNEY A. DIAMOND

Commissioner of Patents and Trademarks